United States Patent
Griesmer et al.

(10) Patent No.: US 9,753,153 B2
(45) Date of Patent: Sep. 5, 2017

(54) HIGH SPATIAL RESOLUTION MODE SOLID STATE POSITRON EMISSION TOMOGRAPHY (PET) SCANNER

(71) Applicant: KONINKLIJKE PHILIPS N.V., Eindhoven (NL)

(72) Inventors: Jerome John Griesmer, Mentor, OH (US); Thomas Leroy Laurence, North Royalton, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 147 days.

(21) Appl. No.: 14/416,070

(22) PCT Filed: Jul. 15, 2013

(86) PCT No.: PCT/IB2013/055819
§ 371 (c)(1),
(2) Date: Jan. 21, 2015

(87) PCT Pub. No.: WO2014/020471
PCT Pub. Date: Feb. 6, 2014

(65) Prior Publication Data
US 2015/0192685 A1   Jul. 9, 2015

Related U.S. Application Data

(60) Provisional application No. 61/677,203, filed on Jul. 30, 2012.

(51) Int. Cl.
*G01T 1/208*   (2006.01)
*G01T 1/164*   (2006.01)
(Continued)

(52) U.S. Cl.
CPC ............. *G01T 1/208* (2013.01); *A61B 6/037* (2013.01); *G01T 1/1647* (2013.01); *G01T 1/2018* (2013.01); *G01T 1/2985* (2013.01)

(58) Field of Classification Search
CPC ................................ G01T 1/208; A61B 6/037
See application file for complete search history.

(56) References Cited

U.S. PATENT DOCUMENTS 6,180,946 B1   1/2001  Ebstein
2009/0032717 A1   2/2009  Aykac et al.
(Continued)

FOREIGN PATENT DOCUMENTS

WO   2010034619 A1   4/2010
WO   2010140070 A2   12/2010

OTHER PUBLICATIONS

Moses, W. W., et al.; Design of High-Resolution, High-Sensitivity PET Camera for Human Brains and Small Animals; 1997; IEEE Trans. on Nuclear Science; NS-44:1487-1491.
(Continued)

*Primary Examiner* — Yara B Green

(57) ABSTRACT

A positron emission tomography (PET) system (10) and method (100) classifies gamma events. At least one processor (62, 66, 70) is programmed to receive event data for a plurality of scintillation events corresponding to gamma events. The gamma events are generated by gamma photons from a region of interest (ROI) (14). The gamma events of the event data are classified into a plurality of classifications. The classifications distinguish between single-crystal gamma events and multi-crystal gamma events.

15 Claims, 3 Drawing Sheets

(51) Int. Cl.
*G01T 1/29* (2006.01)
*A61B 6/03* (2006.01)
*G01T 1/20* (2006.01)

(56) References Cited

U.S. PATENT DOCUMENTS

2011/0150181 A1  6/2011  Cook et al.
2011/0198504 A1  8/2011  Eigen
2012/0061576 A1  3/2012  Degenhardt et al.

OTHER PUBLICATIONS

Rafecas, M., et al.; Inter-crystal scatter in a dual layer, high resolution LSO-APD positron emission tomograph; 2003; Phys. Med. Biol.; 48:821-848.
Rafecas, M., et al.; Characterization and Processing of Inter-Crystal Scatter in a Dual Layer, High Resolution LSO-APD-PET; 2001; IEEE Nuclear Science Symposium Conf. Record; pp. 1128-1132.
Schmall, J., et al.; Large-area CMOS positron-sensitive solid-state photomultipliers for high resolution multimodality PET/MR imaging; 2012; http://engineering.ucsb.edu/biosymposium/files/UC12.
Sublima; home page; http://www.sublima-pet-mr.eu/ accessed Oct. 2, 2014, published Oct. 28, 2010.

HIGH SPATIAL RESOLUTION MODE SOLID STATE POSITRON EMISSION TOMOGRAPHY (PET) SCANNER

CROSS REFERENCE TO RELATED APPLICATIONS

This application is a national filing of PCT application Serial No. PCT/IB2013/055819, filed Jul. 15, 2013, published as WO 2014/020471 A2 on Feb. 6, 2014, which claims the benefit of U.S. provisional application Ser. No. 61/677,203 filed Jul. 30, 2012, which is incorporated herein by reference.

The present application relates generally to positron emission tomography (PET). It finds particular application in conjunction with generating high resolution images in solid state PET scanners and will be described with particular reference thereto. However, it is to be understood that it also finds application in other usage scenarios and is not necessarily limited to the aforementioned application.

PET scanners typically use photomultiplier tube (PMT) detectors and Anger logic to position gamma events. This 'blurs' how the gamma photons interact with the crystal layer and leads to information loss. 60% of the 511 keV gamma photons undergo Compton scatter. About half of these gamma events complete the energy deposition in a single crystal. The remaining gamma events, about 30%, complete the energy deposition in two or more crystals.

With the advent of solid state sensors, such as silicon photo multipliers, additional information about how the gamma photons interact with the crystal layer is available. This additional information allows identification of single and multi-crystal Compton events. For multi-crystal events, the energy detected by each pixel must typically undergo 'clustering' to put the Compton scatter back 'together'. This is done by checking the 'singles' timestamps within a detector module and checking for timestamps within the 'cluster window'. If two or more pixels have timestamps within that window, the energies of these pixels are added to get a combined total energy, and an appropriate algorithm is used to assign a location to that energy.

Beyond identification of single and multi-crystal Compton events, the additional information also allows identification of low energy photon (LEP) light sharing. Even when all of the gamma energy is dumped into a single crystal, there can be a small amount of LEP 'light leakage' of the crystal light to adjacent pixels, depending on the reflector geometry used. Statistical profiling during calibration can distinguish between LEP light sharing and Compton events.

During reconstruction, known solid state PET systems take in to account multi-crystal Compton events, which account for about 30% of gamma events. If these gamma events were discarded, the overall system sensitivity would drop to $(1-0.3)^2=0.49$ or 49% of a standard PET with PMT and Anger logic, which is generally unacceptable. However, in some instances, it would be desirable to discard multi-crystal Compton events during reconstruction, since taking in to account multi-crystal gamma events leads to error in spatial reconstruction. Namely, the energy level of a deposition is not an indicator of which crystal was hit first. As such, the point of initial crossing of the crystal entrance face is indeterminate within a few crystals.

The present application provides a new and improved system and method which overcome the above-referenced problems and others.

In accordance with one aspect, a positron emission tomography (PET) system is provided. The system includes at least one processor programmed to receive event data for a plurality of scintillation events corresponding to gamma events. The gamma events are generated by gamma photons from a region of interest (ROI). The processor then classifies the gamma events of the event data into a plurality of classifications. The classifications distinguish between single-crystal gamma events and multi-crystal gamma events.

In accordance with one aspect, a positron emission tomography (PET) method is provided. The method includes receiving event data for a plurality of scintillation events corresponding to gamma events. The gamma events are generated by gamma photons from a region of interest (ROI). The method further includes classifying the gamma events of the event data into a plurality of classifications. The classifications distinguish between single-crystal gamma events and multi-crystal gamma events.

In accordance with another aspect, a positron emission tomography (PET) system is provided. The system includes a plurality of solid state detector modules receiving gamma photons from a region of interest and generating event data for a plurality of scintillation events corresponding to gamma events generated by the gamma photons. Each of the plurality of solid state detectors includes a plurality of opto-electric tranducers optically coupled in a 1:1 ratio with a plurality of scintillation crystals. The opto-electric tranducers detect the scintillation events, where the scintillation events generated in the scintillation crystals. The system further includes at least one processor programmed to receive the event data for the scintillation events. Further, the processor classifies the gamma events of the event data into a plurality of classifications. The classifications distinguish between single-crystal gamma events and multi-crystal gamma events.

One advantage resides in increased spatial resolution.

Another advantage resides in multiple modes of reconstruction.

Another advantage resides in a raw listmode file.

Another advantage resides in event data annotated with the amount of Compton scatter.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
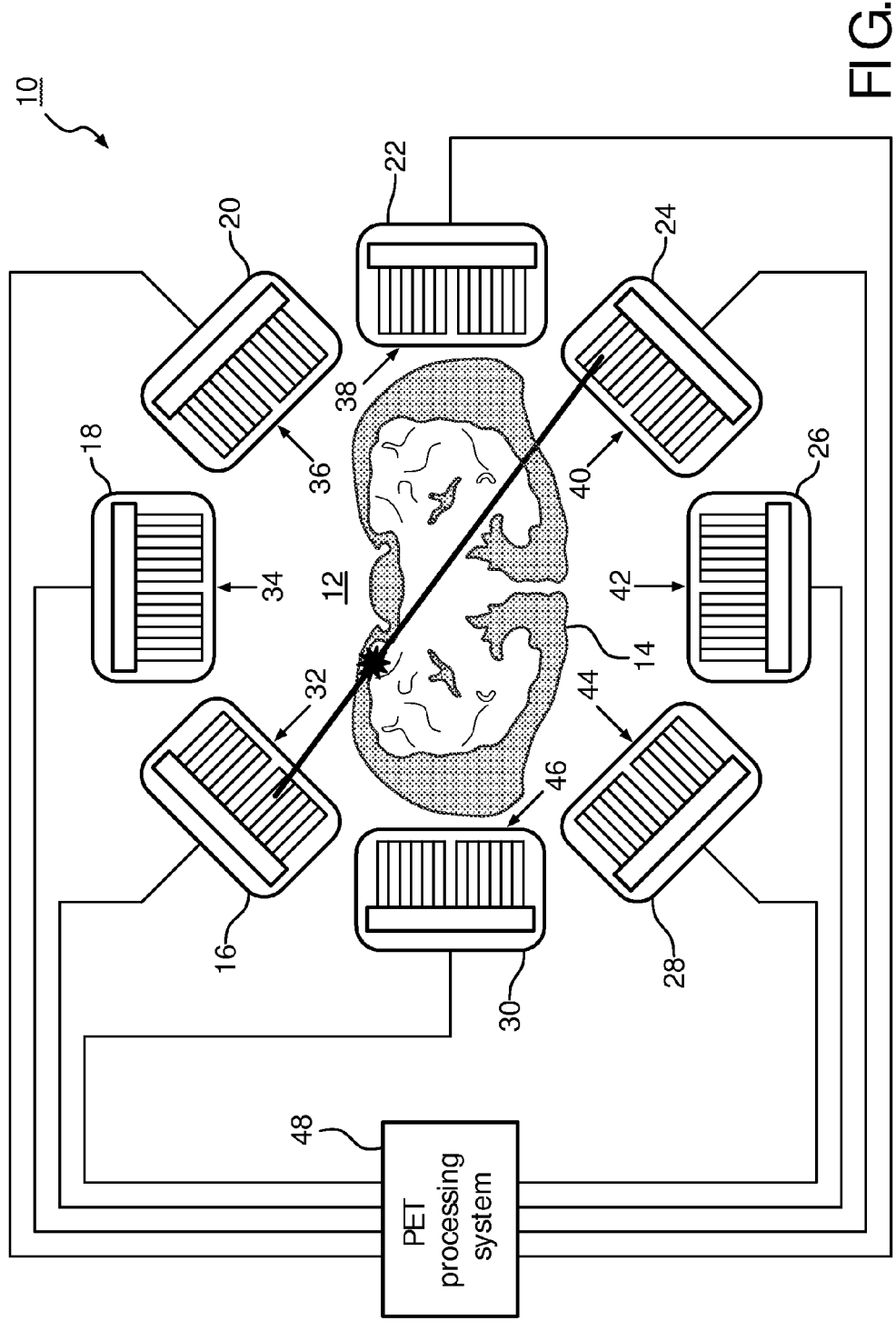
FIG. 1 illustrates a positron emission tomography (PET) system employing solid state detector modules.

With reference to FIG. 1, a positron emission tomography (PET) system 10 includes an imaging volume 12 for receiving a region of interest (ROI) 14 of a patient to image. Further, the PET system 10 can include a patient support (not shown), such as a patient bed, to support the patient and/or position the ROI 14 in the imaging volume 12. Examples of the ROI 14 include, but are not limited to, hearts, brains, thyroids, bones, joints, ligaments, tendons, muscles, nerves, kidneys, lungs, tumors, lesions, and so on.

The PET system 10 further includes a plurality of solid state detector modules 16, 18, 20, 22, 24, 26, 28, 30 arranged, typically in a circle, around the imaging volume 12. The detector modules 16, 18, 20, 22, 24, 26, 28, 30 include receiving faces 32, 34, 36, 38, 40, 42, 44, 46 for receiving gamma photons from the imaging volume 12. In response to receiving gamma photons, the detector modules 16, 18, 20, 22, 24, 26, 28, 30 generate event data for the gamma events, which is provided to a PET processing system 48 of the PET system 10. The gamma events are typically single crystal and/or multi-crystal events. As illustrated a pair of gamma photons are emitted from the ROI 14 and strike a first detector module 16 and a second detector module 24 near simultaneously (i.e., coincident).

Figure 2:
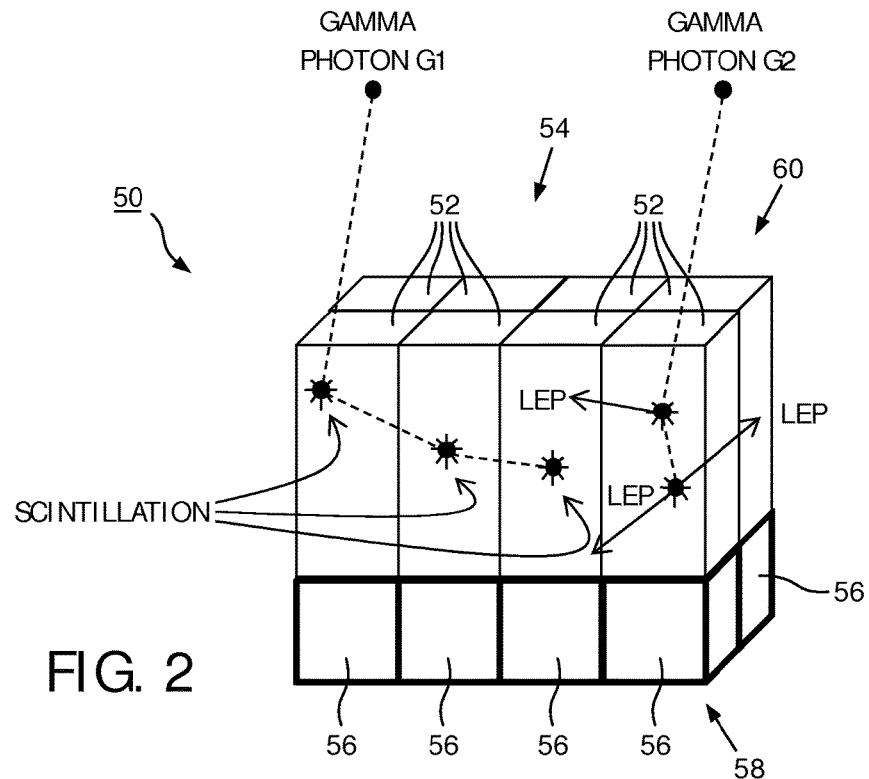
FIG. 2 illustrates at least a portion of a detector module.

With reference to FIG. 2, each 50 of the detector modules 16, 18, 20, 22, 24, 26, 28, 30 includes a plurality of scintillator elements 52 which typically define the receiving face 54 of the detector module 50. The scintillator elements 52 are optically coupled with a plurality of light sensitive elements 56. Typically, the scintillator elements 52 are optically coupled in a 1:1 ratio with the light sensitive elements 56. When a gamma photon deposits energy in the scintillator elements 52, the scintillator elements 52 scintillate and emit visible-light photons toward the light sensitive elements 56. The amount of energy or light created by the scintillation event is directly correlated to amount of energy deposited. Further, the gamma photon may be scattered or deflected. This change in trajectory is defined by the scatter or Compton angle. The amount of energy deposited is proportional to the scatter or Compton angle. In the illustrated example, a gamma photon G1 is scattered in two scintillator elements before finally depositing the remainder of its energy in a third scintillator element causing three scintillation events in three different scintillator elements. Examples of scintillation elements include scintillator plates (e.g., sodium iodide crystals), individual scintillation or pixelated crystals (e.g., LYSO, LSO, etc.), and the like.

The light sensitive elements 56 detect scintillation events, and the energy of scintillation events, by counting photons emitted by the scintillation events. When one of the light sensitive elements 56 detects at least a predetermined number of photons within a time window, it triggers. In the illustrated example, a gamma photon G2 deposits all of its energy in a single crystal and a scintillation event is detected by a single light sensitive element. However, due to low energy photon (LEP) light sharing, a plurality of light sensitive elements may sense a scintillation event. LEP light sharing occurs when gamma energy deposited in a scintillation element is detected by a light sensitive element other than the light sensitive element corresponding to the scintillation element. A small amount of light traverses the reflective coatings on the surfaces of the scintillator elements 52 and enters a neighboring scintillation element. The neighboring scintillation element functions as a light guide to channel the light to its corresponding light sensitive element. Further, the light sensitive elements 56 define a pixelated detection grid 58, where each of the light sensitive elements 56 corresponds to a different pixel of the pixelated detection grid 58. The pixelated detection grid 58 can be subdivided into a plurality of non-overlapping blocks, such as block 60, each block comprised of a grouping of pixels, such as a 2×2 grouping of pixels. Examples of light sensitive elements include digital or analog silicon photomultipliers (SiPMs), photodiodes, and other opto-electric transducers.

The detector module 50 uses the light sensitive elements 56 to create event data for gamma events. The event data for the gamma events describes the corresponding scintillation events detected by the light sensitive elements 56. The event data for each scintillation event identifies the one or more light sensitive elements detecting the scintillation event, the energy detected by the light sensitive elements detecting the scintillation event, and the time of the scintillation event. Low levels of LEP light sharing may not be sufficient for the neighboring light sensitive elements to trigger. However, failure to identify the energies of LEPs leaking into neighboring scintillation element leads to underestimating the energy of gamma events during reconstruction. Hence, the event data for each scintillation event can further identify the energy detected by the one or more light sensitive elements neighboring the light sensitive element detecting the scintillation event.

Figure 3:
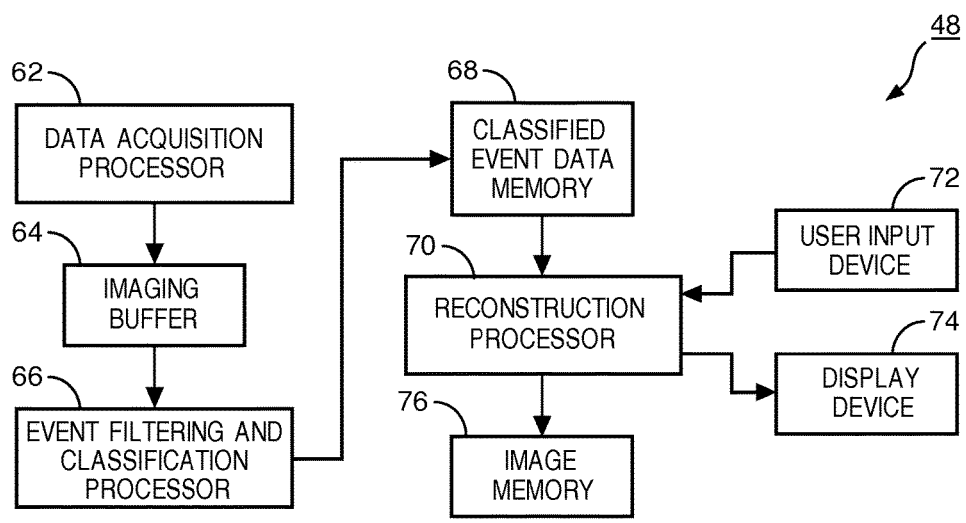
FIG. 3 illustrates a PET processing system.

Referring to FIG. 3, the PET processing system 48 includes a data acquisition processor 62. The data acquisition processor 62 acquires event data for imaging the ROI 14 from the detector modules 16, 18, 20, 22, 24, 26, 28, 30 over a data acquisition period of a predetermined length, such as several milliseconds. The event data includes event data for all the scintillation events detected by the detector modules 16, 18, 20, 22, 24, 26, 28, 30 during the data acquisition period. The data acquisition processor 62 further stores the acquired event data in an imaging buffer 64. The imaging buffer 64 does not need to store event data for a whole image.

In preparing for the acquisition, the ROI 14 is injected with one or more radioisotopes. Examples of such radioisotopes include, but are not limited to, F 18, Rb 82, C 11, O 15, and the like. The radioisotopes can be combined and injected with radioligands to create a radiopharceutical that binds to or is preferentially absorbed by specific types of tissue. Further, the ROI 14 is positioned in the imaging volume 12. For example, the patient is positioned on the patient support and the patient support moves the ROI 14 into the imaging volume 12.

An event filtering and classification processor 66 of the PET processing system 48 receives event data for imaging the ROI 14 from the data acquisition processor 62, typically via the imaging buffer 64. Using the received event data, the event filtering and classification processor 66 updates the event data by filtering out invalid gamma events of the event data and flagging the remaining gamma events of the event data with a classification based on the 'amount' of inter-crystal Compton scatter. The remaining gamma events can, for example, be classified as depositing the gamma energy in one of: 1) a single crystal; 2) two adjacent crystals; 3) two non-adjacent crystals; and 4) more than two crystals. The event classification processor 66 further stores the updated event data in a classified event data memory 68. The event data and classification can be stored using, for example, a listmode file.

Figure 4:
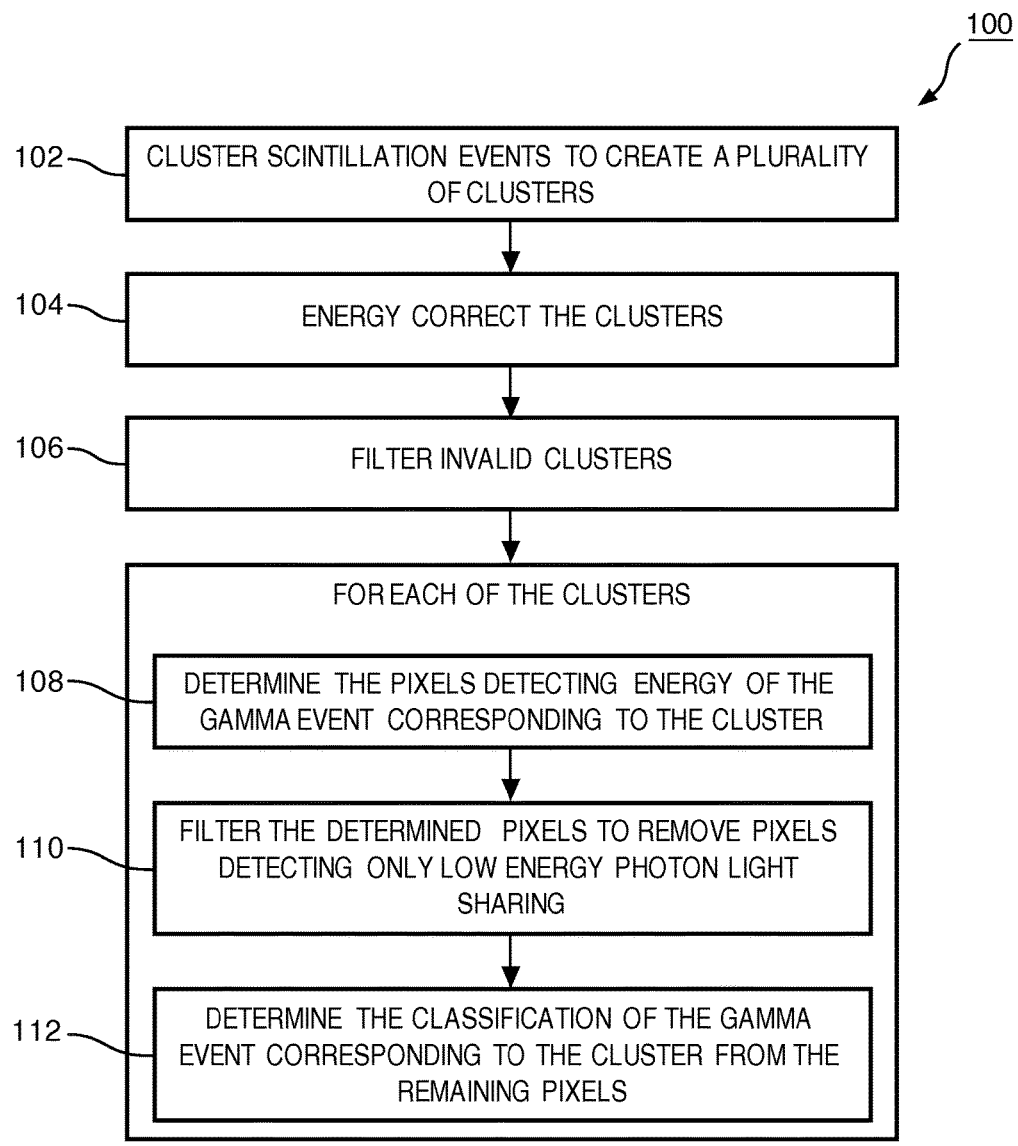
FIG. 4 illustrates a block diagram of a method for filtering and classifying gamma events.

With reference to FIG. 4, the event classification processor 66 is programmed to perform a method 100. The method 100 includes clustering 102 the scintillation events of the event data based on time and detector module to create a plurality of clusters, one for each of the gamma events. This includes, for each of the detector modules corresponding to the gamma events, clustering the scintillation events corresponding to the detector module based on the times of the scintillation events to create one or more of the clusters. Each of the clusters corresponds to a different one of the gamma events and includes the one or more detected scintillation events of the gamma event.

The clusters can optionally be energy corrected 104. Energy correction is important since energy of a gamma event can span a variable number of light sensitive elements. Energy correction ensures all combinations of light sensitive elements maintain a consistent energy peak, such as 511 keV.

Further, the clusters (as energy corrected, where applicable) are filtered 106 to remove clusters corresponding to gamma events with energies outside a target energy window, such as about 511 keV. This includes, for each of the clusters, summing the energies detected by the light sensitive elements of the cluster. Thereafter, the sum is compared to the target energy window to determine whether the sum falls within the target energy window. Insofar as the sum falls outside of the target energy window, the cluster is filtered out.

For each of the remaining clusters, the pixels detecting energy of the gamma event corresponding to the cluster are determined 108. As noted above, the event data for a scintillation event identifies the one or more light sensitive elements detecting the scintillation event and the energy detected by the light sensitive elements detecting the scintillation event. Further, the event data for the scintillation event can identify the energy detected by the other light sensitive elements of the one or more blocks corresponding to the light sensitive elements detecting the scintillation event. Since the light sensitive elements correspond to pixels, the pixels of the cluster can be determined through analysis of the event data for the scintillation events of the cluster.

The determined pixels can optionally be filtered 110 to remove pixels corresponding only to light sensitive elements which detected LEP light sharing. Statistical profiling during calibration can be employed to identify LEP light sharing. For example, if the detected energy of a light sensitive element is less than a predetermined amount, the light sensitive element detected LEP light sharing.

Next, the remaining pixels are analyzed to determine 112 a classification for the gamma event corresponding to the cluster. If the remaining pixels include only a single pixel, the gamma energy of the gamma event corresponding to the cluster was deposited within a single crystal. If the remaining pixels include more than two pixels, the gamma energy of the gamma event corresponding to the cluster was deposited within more than two crystals. If the remaining pixels include one of two adjacent pixels and two non-adjacent pixels, the gamma energy of the gamma event corresponding to the cluster was deposited within one of two adjacent crystals and two non-adjacent crystals, respectively.

The classification performed by the event classification processor 66 can additionally or alternatively include flagging each of the gamma events as depositing the gamma energy in one of: 1) a single crystal; 2) two adjacent crystals within a block; 3) two adjacent crystals in different blocks; and 4) any other combination. As discussed above, a block is a subdivision, typically a 2×2 grouping of pixels, of a pixelated detection grid of a detector module. The method 100 described by FIG. 4 can be employed for performing this classification through modification of the determination 112 of the classification to include the following logic.

If the remaining pixels only include a single pixel, the gamma energy of the gamma event corresponding to the cluster was deposited within a single crystal. If the remaining pixels share a common block and are adjacent, the gamma energy of the gamma event corresponding to the cluster was deposited in two adjacent crystals within a block. If the remaining pixels are adjacent, but do not share a common block, the gamma energy of the gamma event corresponding to the cluster was deposited in two adjacent crystals in different blocks. If the remaining pixels do not meet any of the foregoing, the gamma energy of the gamma event corresponding to the cluster was deposited in some other combination of crystals.

Referring back to FIG. 3, a reconstruction processor 70 of the PET processing system 48 receives classified event data for imaging the ROI 14, typically via the classified event data memory 68, and generates one or more image representations of the ROI 14. Further, the reconstruction processor 70 receives a selection of one of a plurality of reconstruction modes and, optionally, parameters associated with the selected reconstruction mode to control the generation of the image representation. The selection is performed by, for example, a user of the reconstruction processor 70 using a user input device 72 of the PET processing system 48. Further, the selection can be facilitated with a user interface presented to the user on, for example, a display device 74 of the PET processing system 48.

The reconstruction modes include a 'normal' mode, which uses all valid gamma event pairs or LORs for reconstruction, and a 'high resolution' mode, which uses only single crystal gamma events for reconstruction. The 'high resolution' mode has about half the sensitivity of the 'normal' mode, but has no spatial 'blurring' due to miss identified gamma entrance locations. The reconstruction modes can further include a 'hybrid' mode, which combines the 'normal' mode and the 'high resolution' mode through selective weighting.

To generate a 'normal' or 'high resolution' mode image representation, the reconstruction processor 70 filters the gamma event pairs or LORs based on the on the selected reconstruction mode and reconstructs the remaining gamma event pairs or LORs into the image representation. For example, if the 'high resolution' mode is selected, all gamma event pairs or LORs based on one or more multi-crystal gamma events are filtered out of the classified event data and the image representation is reconstructed from the remaining gamma event pairs or LORs.

To generate a 'hybrid' image representation, the reconstruction processor 70 generates both 'normal' and 'high resolution' mode images representations from the classified event data. Thereafter, the two images are combined by weighting, for example, on a pixel-by-pixel basis. The relative weights of the two images can be selected during selection of the reconstruction mode. Alternatively, the reconstruction processor 70 weights each LOR based on the classification of the pair of events that define the LOR to generate the 'hybrid' image representation. For a higher resolution image, LORs defined by only single crystal events are weighted more heavily than LORs defined by multi crystal events, which are weighted less heavily. The greater the number of crystals the event is scattered over, the less the weighting. To generate an image with improved noise statistics with less spatial resolution, the scattered events are weighted more heavily. Equal weighting of all events is used to create a normal image.

While not necessarily, in some embodiments, the reconstruction processor 70 uses 'prior' information to help 'focus' the use of the classified event data. For example, the 'high resolution' image can be used as a 'prior' for the rest of a reconstruction process (e.g., to generate a 'normal' image representation), thus maintaining full 'sensitivity' for the scan data.

The reconstruction processor 70, in addition to generating the image representations, such as a 'high resolution' image representation and/or a 'normal' image representation, typically stores the image representations in an image memory 76 of the PET processing system 48 for subsequent use. Alternatively, the list mode data is stored. For example, the image representations can be employed by a video processor and/or displayed on a display device, such as the display device 74. In displaying the image representations, the image representations can, for example, be displayed side-by-side. It is also contemplated that the reconstruction processor 70 can generate one or more sonograms, such as photo peak and/or Compton sinograms.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes at least one memory and at least one processor, the processor executing processor executable instructions on the memory; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A positron emission tomography (PET) system, said system comprising:
   at least one processor programmed to:
      receive event data for a plurality of scintillation events corresponding to gamma events, the gamma events generated by gamma photons from a region of interest (ROI);
      cluster the scintillation events based on time to create a plurality of clusters, each cluster corresponding to a different one of the gamma events;
      determine a classification of the gamma event corresponding to each cluster based on a spatial configuration and a number of each cluster, the classifications distinguishing between single-crystal gamma events and multi-crystal gamma events, wherein the classifications indicate whether gamma energy was deposited in: 1) a single crystal; 2) two adjacent crystals; 3) two non-adjacent crystals; and 4) more than two crystals;
      generate a first image representation of the ROI using only single-crystal gamma events;
      generate additional image representations of the ROI corresponding to the classifications;
      weight each additional image representation based on the classification; and,
      combine the first image and the weighted additional images to generate the image representation of the ROI.

2. The positron emission tomography (PET) system according to claim 1, wherein the classifications indicate whether gamma energy was deposited in: 1) a single crystal; 2) two adjacent crystals; 3) two non-adjacent crystals; and 4) more than two crystals.

3. The PET system according to claim 1, further including:
   a display configured to display the image representation of the ROI.

4. The PET system according to claim 1, further including:
   a plurality of detectors, each detector includes a plurality of opto-electric transducers optically coupled in a 1:1 ratio with a plurality of scintillation crystals, the opto-electric transducers detecting scintillation events generated in the scintillation crystals by the gamma photons.

5. A positron emission tomography (PET) system, the system comprising:
   at least one processor programmed to:
      receive event data for a plurality of scintillation events corresponding to gamma events, the gamma events generated by gamma photons from a region of interest (ROI);
      generate lines of response corresponding to pairs of coincident gamma events, each radiation event being generated based on light from one or more crystals of a radiation detector;
      cluster the scintillation events based on time to create a plurality of clusters, each cluster corresponding to a different one of the gamma events;
      determine the one or more crystals detecting each gamma event corresponding to the cluster;
      classify the gamma event corresponding to each cluster based on a spatial configuration and a number of the determined crystals;
      weight each line of response based on the classifications of its pair of concurrent gamma events; and
      generate an image representation of the ROI using the weighted lines of response, wherein a weight given to a line of response decreases as the number of crystals the pair of gamma events spans increases.

6. The PET system according to claim 5, further including:
   a device display configured to display the image representation of the ROI.

7. A positron emission tomography (PET) method, comprising:
   with one or more computer processors, clustering scintillation events based on time to create a plurality of clusters, each cluster corresponding to a different one of the gamma events;
   with the one or more computer processors, for each of the clusters:
      receiving event data for a plurality of scintillation events corresponding to the gamma events, the gamma events generated by gamma photons from a region of interest (ROI),
      determining pixels detecting energy of the gamma event corresponding to the cluster;
      classifying the gamma events corresponding to each cluster into a plurality of classifications based on a spatial configuration and a number of the determined pixels over which the gamma events of the cluster are distributed;
      generating lines of response corresponding to pairs of concurrent gamma events,
      determining weighting for each of the classifications, and one of:
         reconstructing a plurality of images corresponding to the classifications, weighting each image based on the weightings of the corresponding classification, combining the weighted images to generate an image representation of the ROI, or weighting each line of response based on the classifications of the corresponding pair of gamma events and reconstructing the weighted lines of response to generate an image representation of the ROI.

8. The PET method according to claim 7, further including:

with a display device, displaying the image representation of the ROI.

9. The PET method according to claim 7, wherein the weighting of the gamma events decreases as the number of crystals the gamma event spans increases.

10. The PET method according to claim 7 wherein the classifications indicate of whether gamma energy was deposited in: 1) a single crystal; 2) two adjacent crystals; 3) two non-adjacent crystals; and 4) more than two crystals.

11. A non-transitory computer-readable medium carrying software configured to control a computer processor to perform the PET method according to claim 7.

12. The PET method according to claim 10, wherein the image of the ROI is generated with a hybrid mode, and wherein the image of the ROI includes:

generating a first image representation of the ROI using only single-crystal gamma events of the gamma events;

generating a second image representation of the ROI using the gamma events deposited in two crystals;

generating a third image representation using all of the gamma events;

weighting the first image representation with a weighting determined for the single-crystal gamma event classification;

weighting the second image representation with a weighting determined for the two-crystal gamma event classification;

weighting the third image representation with a weighting determined for the more than two-crystal gamma event classification; and, combining the weighted first, second, and third images to generate the image representation of the ROI.

13. A positron emission tomography (PET) system for classifying gamma events, said system comprising:

a plurality of detector modules receiving gamma photons from a region of interest (ROI) and generating event data for a plurality of scintillation events corresponding to gamma events generated by the gamma photons, wherein each of the plurality of detectors includes a plurality of opto-electric transducers optically coupled in a 1:1 ratio with a plurality of scintillation crystals, the opto-electric transducers detecting the scintillation events, the scintillation events being generated in the scintillation crystals; and, at least one processor programmed to:

receive the event data for the scintillation events;

classify the gamma events of the event data into a plurality of classifications, each classification indicating one of single-crystal gamma events, gamma events spanning two crystals, and gamma events spanning more than two crystals;

determine lines of response extending between a pair of coincident gamma events;

weight each line of response based on the classifications of the pair of coincident gamma events; and reconstruct the weighted lines of response into the image representation of the ROI.

14. The PET system according to claim 13, where the processor is further programmed to:

receive a selection of one of a plurality of reconstruction modes, the selection associated with one or more of the classifications; and, generate an image representation of the ROI and/or a sinogram using only gamma events corresponding to the classifications associated with the selected reconstruction mode and further including:

a display device configured to display the image representation of the ROI.

15. A positron emission tomography (PET) system for classifying gamma events, said system comprising:

a plurality of detector modules receiving gamma photons from a region of interest (ROI) and generating event data for a plurality of scintillation events corresponding to gamma events generated by the gamma photons, wherein each of the plurality of detectors includes a plurality of opto-electric transducers optically coupled in a 1:1 ratio with a plurality of scintillation crystals, the opto-electric transducers detecting the scintillation events, the scintillation events generated in the scintillation crystals; and, at least one processor programmed to:

receive the event data for the scintillation events;

classify the gamma events of the event data into a plurality of classifications, each classification indicating one of single-crystal gamma events, gamma events spanning two crystals, and gamma events spanning more than two crystals;

reconstruct a first image based on the single-crystal gamma events;

generate a second image based on gamma events spanning up to two crystals;

reconstruct a third image representation based on all gamma events;

weight each of the first, second, and third images with weighting factors corresponding to the single-crystal events, gamma events spanning up to two crystals, and all gamma events, respectively; and combine the weighted first, second, and third images to generate an image representation of the ROI.

* * * * *